United States Patent
Gardner et al.

(10) Patent No.: US 6,984,756 B2
(45) Date of Patent: Jan. 10, 2006

(54) PROCESS FOR PREPARING BIPHENYL COMPOUNDS

(75) Inventors: John Paul Gardner, Indianapolis, IN (US); William David Miller, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 269 days.

(21) Appl. No.: 10/258,264

(22) PCT Filed: May 4, 2001

(86) PCT No.: PCT/US01/11745

§ 371 (c)(1),
(2), (4) Date: Oct. 18, 2002

(87) PCT Pub. No.: WO01/90055

PCT Pub. Date: Nov. 29, 2001

(65) Prior Publication Data

US 2003/0092947 A1 May 15, 2003

Related U.S. Application Data

(60) Provisional application No. 60/205,982, filed on May 19, 2000.

(51) Int. Cl.
*C07C 303/40* (2006.01)

(52) U.S. Cl. ......................................................... 564/82

(58) Field of Classification Search ................... 564/82
See application file for complete search history.

(56) References Cited

U.S. PATENT DOCUMENTS 6,303,816 B1    10/2001    Arnold et al. ................ 564/82

FOREIGN PATENT DOCUMENTS

| WO | WO 00/06537 | 7/1998 |
| WO | WO 01/90057 | 5/2000 |

OTHER PUBLICATIONS

N. Miyaura et al: *Chem. Rev.* vol. 95, No. 7, 1995, pp. 2457–2483, XP000652239.
N. Miyaura et al: *Synth. Commun.* vol. 11, No. 7, pp. 513–519, XP000563089.

*Primary Examiner*—Peter O'Sullivan
(74) *Attorney, Agent, or Firm*—Danica Hostettler; Nelsen L. Lentz; John A. Cleveland, Jr.

(57) ABSTRACT

The present invention relates to a process for the preparation of a biphenyl compound comprising combining a phenyl boronic acid derivative with an halobenzene derivative in the presence of a suitable additive in a suitable organic solvent with a suitable catalyst and a suitable base.

17 Claims, No Drawings

PROCESS FOR PREPARING BIPHENYL COMPOUNDS

This is the national phase application, under 35 USC 371, for PCT/US01/11745, filed 04 May 2001, which claims the priority of U.S. Provisional Application No. 60/205,982 filed 19 May 2000.

A review by Akira Suzuki discloses in the *Journal of Organometallic Chemistry*, 576, 147–168 (1998) recent advances in the cross-coupling reactions of organoboron derivatives with organic electrophiles. In addition, a review by Miyaura and Suzuki further disclose in *Chemical Reviews*, 95, 2457–2483 (1995) palladium-catalyzed cross-coupling reactions of organoboron compounds.

The present invention provides a process for the preparation of a biphenyl compound comprising combining a phenyl boronic acid derivative with a suitable benzene derivative in the presence of a suitable additive in a suitable organic solvent with a suitable catalyst and a suitable base.

The present invention further provides a process for the preparation of a compound of formula I:

formula I

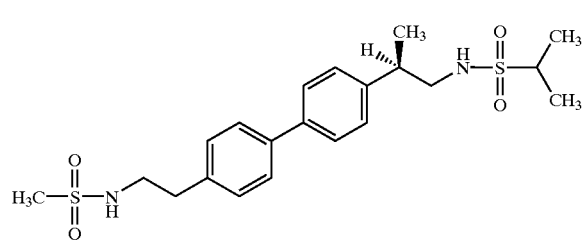

comprising combining a compound of the formula (13):

(13)

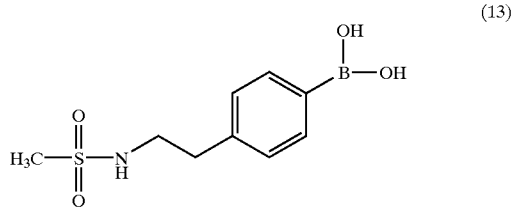

with a compound of the formula (6):

(6)

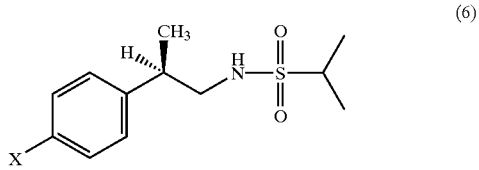

wherein X represents Hal or triflate, in the presence of a suitable additive in a suitable organic solvent with a suitable catalyst and a suitable base.

The present invention further provides a process for reducing the levels of achiral dimer of the formula:

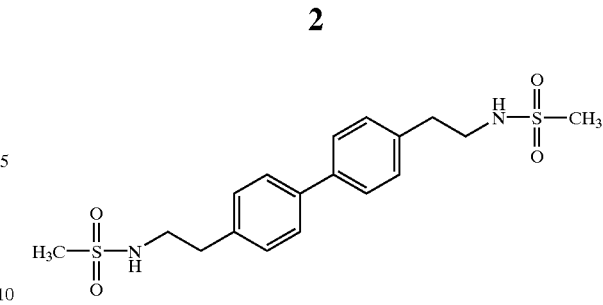

which stubbornly persists as a byproduct in the formation of the compound of formula I:

formula I

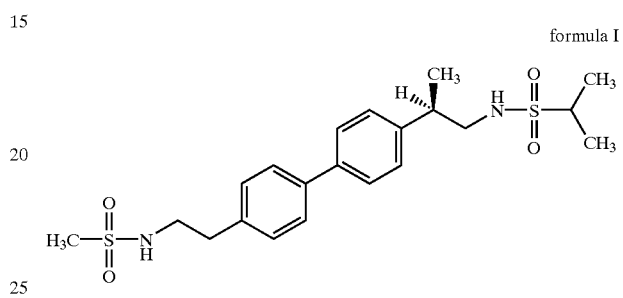

comprising recrystallization of a mixture of the achiral dimer and the compound of formula I from a suitable solvent system.

The present invention further provides a process for significantly reducing the levels of achiral dimer and chiral dimer of the formula:

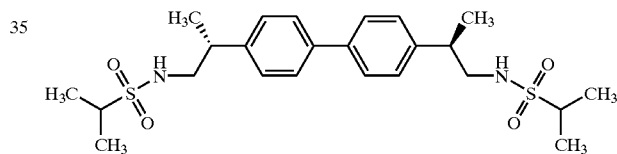

which are produced as byproducts in the formation of the compound of formula I:

formula I

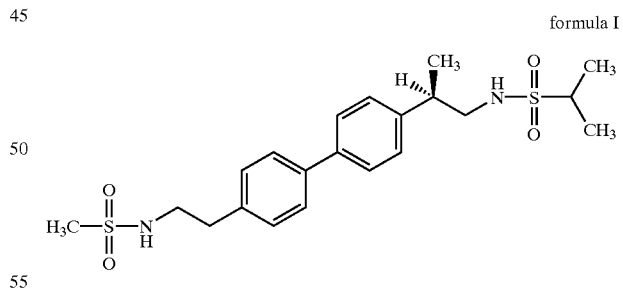

comprising recrystallization of a mixture of the achiral dimer, chiral dimer, and the compound of formula I from a suitable solvent system.

DETAILED DESCRIPTION OF THE INVENTION

As used herein the name "{(2R)-2-[4-(4-{2-[(methylsulfonyl)amino]ethyl}phenyl)phenyl]propyl}[(methylethyl)sulfonyl]amine" refers to the compound of formula I:

formula I

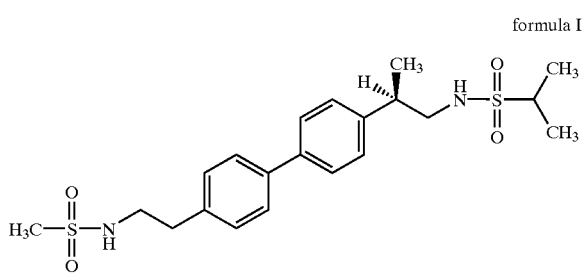

A used herein the name "achiral dimer" refers to "methylsulfonyl){2-[4-(4-{2-[methylsulfonyl)amino]ethyl}phenyl)phenyl]ethyl}amine" and is represented by the following structure:

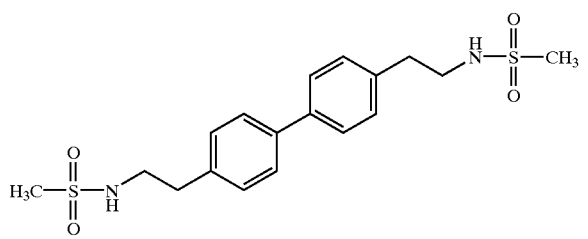

A used herein the name "chiral dimer" refers to "((2R)-2-{4-[4-((1R)-1-methyl-2-{[(methylethyl)sulfonyl]amino}ethyl)phenyl]phenyl}propyl)[methylethyl)sulfonyl]amine" and is represented by the following structure:

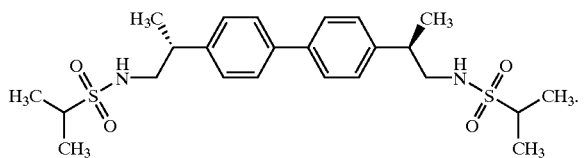

The present invention includes the pharmaceutically acceptable salts of the compounds defined by formula I. The term "pharmaceutically acceptable salt" as used herein, refers to salts of the compounds of the above formula which are substantially nontoxic to living organisms. Typical pharmaceutically acceptable salts include those salts prepared by reaction of the compounds of the present invention with a pharmaceutically acceptable organic or inorganic base. Such salts are known as base addition salts. Such salts include the pharmaceutically acceptable salts listed in *Journal of Pharmaceutical Science*, 66, 2–19 (1977) which are known to the skilled artisan.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, calcium methoxide, magnesium hydroxide, magnesium carbonate, magnesium methoxide, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" referes to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein the term "biphenyl compound" refers to any substituted biphenyl or an unsubstituted biphenyl. For example, an unsubstituted biphenyl is represented by the following structure:

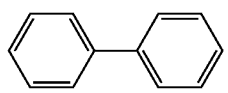

and a substituted biphenyl is represented by, but not limited to, the following structure:

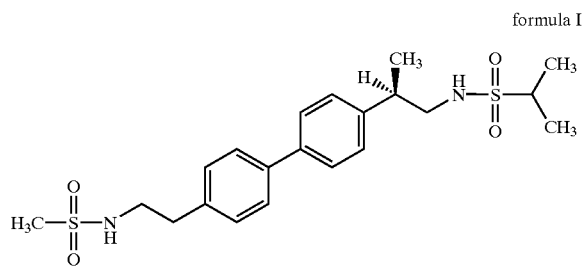

formula I

As used herein the term "phenyl boronic acid derivative" refers to any substituted phenyl boronic acid or an unsubstituted phenyl boronic acid. For example, an unsubstituted phenyl boronic acid derivative is represented by the following structure:

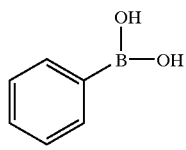

and a substituted boronic acid derivative may be represented by, but not limited to, the following structure:

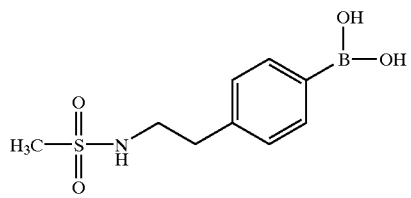

(13)

As used herein the term "suitable benzene derivative" refers to any substituted benzene or an unsubstituted benzene. For example, an unsubstitued benzene may be represented by the following structure:

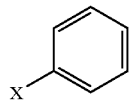

and a substituted benzene derivative may be represented by, but not limited to, the following structure:

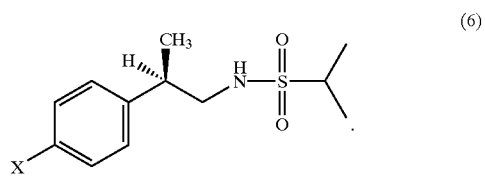

(6)

wherein X represents Hal or triflate.

As used herein the terms "Hal", "halo", "halogen" or "halide" refers to a chlorine, bromine or iodine atom, with iodine being preferred.

As used herein the term "triflate" refers to a trifluoromethanesulfonate of formula —OSO$_2$CF$_3$.

As used herein the term "substituted" signifies that one or more substituents may be present on the phenyl or benzene ring, wherein said substituents do not prevent the combination of the phenyl boronic acid derivative and the iodobenzene derivative in the presence of aqueous potassium formate in a suitable organic solvent with a suitable catalyst.

The compounds of formula I can be prepared, for example, following analogous procedures set forth in International Patent Application Publication WO 98/33496 published Aug. 6, 1998 (See Example 51 therein) to prepare the racemate of formula I followed by resolution to provide the desired (R) enantiomer (formula I) or the (S) enantiomer. More specifically, the compounds of formula I can be prepared, for example, following the procedures set forth in Schemes I, II, III, and IIIA. The reagents and starting materials are readily available to one of ordinary skill in the art. All substituents, unless otherwise specified are as previously defined.

Scheme I

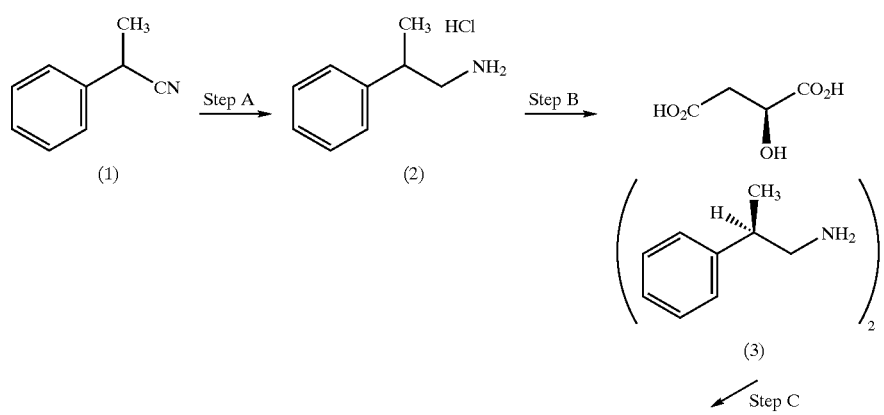

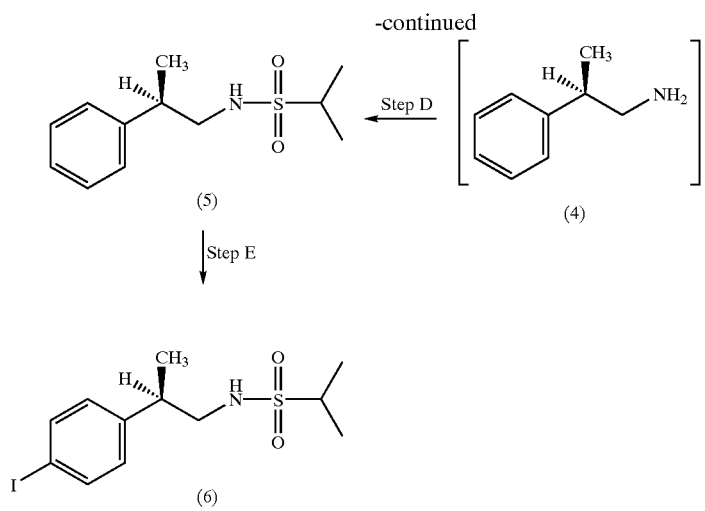

In Scheme I, step A, the nitrile (1) is hydrogenated to provide the primary amine (2) as the HCl salt. For example, nitrile (1) is dissolved in a suitable organic solvent, such as ethanol, treated with a suitable hydrogenation catalyst, such as palladium on carbon, treated with concentrated HCl and placed under hydrogen at a pressure and temperature sufficient to effect reduction of the nitrile (1) to the primary amine (2). The reaction is then filtered and the filtrate concentrated to provide crude primary amine (2) as the HCl salt. This crude material is then purified by techniques well known in the art, such as recrystallization from a suitable solvent.

In Scheme I, step B, the primary amine (2) HCl salt can be treated with a suitable resolving agent to provide the salt (3). For example, the primary amine (2) HCl salt is dissolved in a suitable organic solvent, such as ethanol and treated with about an equivalent of a suitable base, such as sodium hydroxide. The reaction is filtered and the filtrate is treated with a suitable resolving agent, such as L-malic acid. For example, about 0.25 equivalents of L-malic acid in a suitable organic solvent, such as ethanol is added to the filtrate. The solution is then heated to about 75° C. and stirred for about 30 minutes. The solution is then allowed to cool slowly with stirring. The precipitate is then collected by filtration, rinsed with ethanol and dried under vacuum to provide the salt (3). The salt (3) is then suspended in a suitable organic solvent, such as ethanol and water is added. The slurry is heated at reflux until the solids go into solution. The solution is then allowed to cool slowly with stirring for about 8 to 16 hours. The suspension is further cooled to about 0 to 5° C. and the salt (3) is collected by filtration. The salt (3) is then rinsed with ethanol and dried at about 35° C.

In Scheme I, step C, salt (3) is converted to the free base (4) and in Step D, free base (4) is sulfonylated to provide sulfonamide (5). For example, salt (3) is slurried in a suitable organic solvent, such as methylene chloride and treated with about 2 equivalents of a suitable base, such as aqueous sodium hydroxide. The mixture is stirred for about one hour and the organic phase is separated. The organic phase is then dried, for example by azeotropic distillation with heptane to provide the free base (4). The dried free base (4) in heptane is then treated, for example, with a catalytic amount of 4-dimethylaminopyridine, an excess of triethylamine and methylene chloride is added to provide total dissolution. The solution is cooled to about 5° C. and treated with about one equivalent of a compound of formula $Lg\text{-}SO_2CH(CH_3)_2$, such as isopropylsulfonyl chloride. The reaction is then allowed to warm to room temperature over about 16 hours. The reaction is then cooled to about 8° C. and treated with 2N aqueous HCl. The organic phase is then separated and washed with water, sodium bicarbonate, dried over anhydrous sodium sulfate, filtered, and concentrated under vacuum to provide sulfonamide (5).

In Scheme I, step E, the sulfonamide (5) is iodinated to provide the compound (6). For example, sulfonamide (5) is dissolved in glacial acetic acid and treated with approximately 1.1 equivalents concentrated sulfuric acid. To this solution is added about 0.2 equivalents $H_5IO_6$ followed by addition of about 0.5 equivalents of iodine. The reaction is then heated to about 60° C. and allowed to stir for about 3 hours. The reaction is then cooled and treated with 10% aqueous $NaHSO_3$. The mixture is then cooled to about 0° C. to about 50° C. and the resulting solids are collected by filtration and rinsed with water. The solids are then dissolved in a suitable organic solvent, such as MTBE and the solution is rinsed with water, saturated sodium bicarbonate, dried over anhydrous magnesium sulfate, filtered, and partially concentrated under vacuum. A suitable organic solvent, such as heptane is then added with slow stirring until crystallization commences. An additional amount of heptane is added and the suspension is allowed to stir for about 8 hours to about 16 hours. The mixture is then cooled to about 0° C. and the solids are collected by filtration and rinsed with heptane to provide the compound (6).

Scheme II

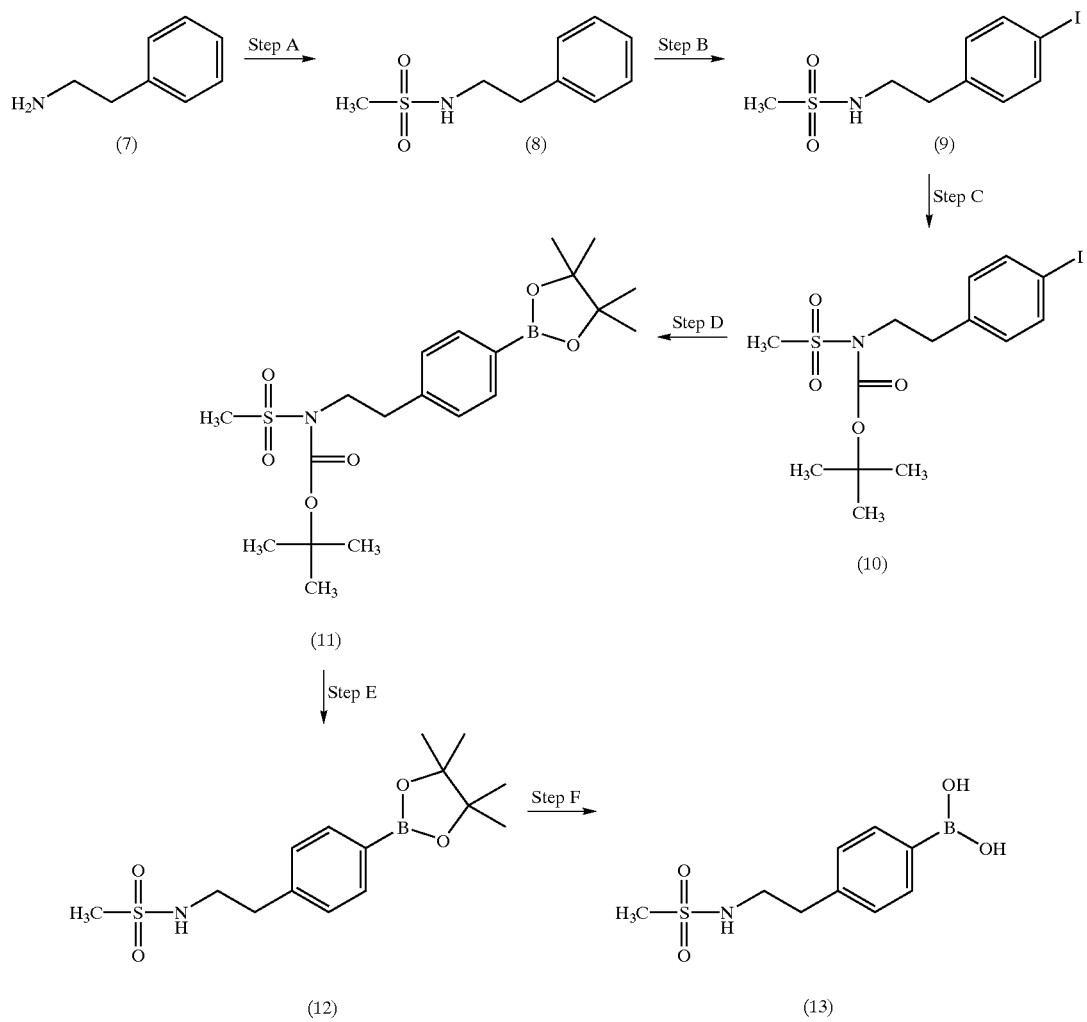

In Scheme II, step A, the primary amine (7) sulfonylated to provide the sulfonamide (8). For example, primary amine (7) is dissolved in a suitable organic solvent, such as methylene chloride and treated with about 1.1 equivalents of triethylamine. The solution is cooled to about 10° C. and treated with about 1.1 equivalents of methanesulfonyl chloride. The solution is then stirred at room temperature for about 1 to 2 hours, washed with 1N HCl and then concentrated under vacuum to provide sulfonamide (8).

In Scheme II, step B, the sulfonamide (8) is iodinated to provide compound (9). For example, sulfonamide (8) is combined with acetic acid, 95% sulfuric acid and water and then treated with about 0.5 equivalents iodine and about 0.2 equivalents periodic acid. The reaction mixture is heated to about 70° C. to about 75° C. for about 3 hours. The reaction mixture is then allowed to stir at room temperature for about 8 hours to about 16 hours. Then about 2 equivalents of base are added such as sodium hydroxide followed by addition of enough saturated sodium sulfite to decolorize the mixture, resulting in a white suspension. The suspension is cooled to about 15° C. and the solids collected by filtration. The solids are then dissolved in a suitable organic solvent, such as methylene chloride, rinsed with water, and the organic phase concentrated under vacuum to provide the compound (9).

In Scheme II, step C, compound (9) is converted to Boc sulfonamide (10). For example, compound (9) is dissolved in a suitable organic solvent, such as methylene chloride and treated with a catalytic amount of 4-dimethylaminopyridine and about 1.2 equivalents of di-tert-butyl dicarbonate. The reaction mixture is then allowed to stir at room temperature for about 8 hours to about 16 hours. The reaction is then rinsed with water and the organic phase is partially concentrated under vacuum. A suitable organic solvent is added, such as hexanes and this solution is again rinsed with water. The organic phase is then concentrated under vacuum and hexanes are added producing a precipitate. The solids are collected by filtration and dried under vacuum to provide Boc sulfonamide (10).

In Scheme II, step D, the Boc sulfonamide (10) is subjected to boronation conditions to provide compound (11). For example, the Boc sulfonamide (10) is dissolved in a suitable organic solvent, such as acetonitrile, and treated with excess triethylamine, a catalytic amount of 1,1'-bis (diphenylphosphino) ferrocenedichloropalladium (II)-

CH$_2$Cl$_2$ complex (0.012 equivalents) and about 1.3 equivalents of pinacolborane. The reaction mixture is allowed to stir at about 70° C. to about 74° C. for about 8 hours. The reaction is then cooled to room temperature and concentrated to a fluid oil. This oil is partitioned between a suitable organic solvent, such as MTBE and water. The organic phase is separated, washed with water and concentrated under vacuum. The residue is partially dissolved in a suitable organic solvent such as heptane. The heptane solution is filtered through Celite® 521 and the filtrated is concentrated under vacuum to provide an oil. The residue is dissolved in a solvent mixture of acetone and heptane and filtered through Celite® 521. The filtrates are concentrated under vacuum to provide compound (11).

In Scheme II, step E, compound (11) is deprotected to provide the compound (12). For example, compound (11) is dissolved in a suitable organic solvent, such as methylene chloride and treated with excess trifluoroacetic acid. The reaction mixture is cooled to about 5° C. and neutralized with aqueous base, such as aqueous sodium hydroxide to provide a pH of the aqueous phase of about 10.5. The phases are separated and the aqueous phase is extracted with a suitable organic solvent, such as methylene chloride. The organic phase and organic extracts are combined, washed with brine, water, diluted with heptane and concentrated under vacuum to provide a suspension. The solids are collected by filtration, rinsed with pentane, and dried under vacuum to provide compound (12).

In Scheme II, step F, compound (12) is subjected to pinacolate cleavage to provide compound (13). For example, compound (12) is combined with 1N ammonium acetate and excess sodium periodate in a suitable organic solvent, such as acetone. The mixture is stirred for about 8 hours to about 16 hours, and then filtered. The solids are rinsed with acetone. The filtrates are combined and concentrated under vacuum to provide a suspension that is collected by filtration. The collected solid is then suspended in water and treated with aqueous sodium hydroxide to provide a pH of about 12.5. The suspension is then filtered and the filtrate treated with decolorizing carbon. The mixture is then filtered and the filtrate is diluted with sulfuric acid until the pH reaches about 5.0. The resulting precipitate is collected by filtration and dried under vacuum to provide compound (13).

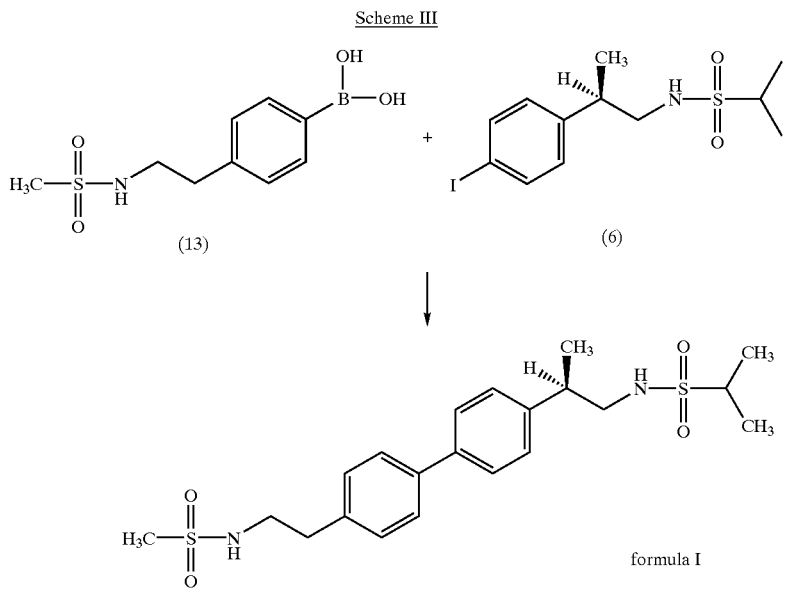

Scheme III

In Scheme III, a phenyl boronic acid derivative, such as compound (13) is coupled to a suitable benzene derivative, such as compound (6) in the presence of a suitable additive in a suitable organic solvent with a suitable catalyst and a suitable base to provide a biphenyl compound, such as the compound of formula I. As used herein the term "suitable additive" refers to additives such as alkali metal and tetraalkylammonium formates, that suppress the production of achiral dimer, or more generally, to suppress the production of symmetric biaryl compounds derived solely from the self-coupling of the phenyl boronic acid derivative. Examples of suitable additives include but are not limited to hydrogen, hydroquinone, isopropanol, and formate salts, such as sodium formate, potassium formate, tetralkylammonium formate, and the like. For example, an aqueous solution of potassium formate is prepared by combining water, potassium hydroxide and one equivalent of 98% formic acid. To this solution is then added about 1.0 equivalents to about 10 equivalents of a suitable base, with about 2.0 equivalents being preferred. Examples of suitable bases are potassium carbonate, sodium carbonate, and the like. About 0.95 equivalents to about 1.0 equivalents of compound (13) are added, with about 0.95 equivalents of compound (13) being preferred. About 0.95 equivalents to about 1.0 equivalents of compound (6) are added, with about 1.0 equivalents of compound (6) being preferrred. A suitable organic solvent is also added to the above mixture. Examples of suitable organic solvents are tetrahydrofuran, C$_1$ to C$_{10}$ branched and straight chain alcohols, such as methanol, ethanol, isopropanol, n-propanol, butanol, t-butanol, pentanol, hexanol, heptanol, octanol, and the like, and ketones, such as acetone, butanone, and the like. It is understood that the above components, including the suitable organic solvent, can be combined in any order. To this mixture, which has been deoxygenated and placed under nitrogen, is added a catalytic amount of a suitable catalyst, such as a palladium (0) catalyst, such as palladium black or palladium on carbon, and again the mixture is deoxygenated and placed under nitrogen. The mixture is then heated at about 88° C. for about 8 hours to about 16 hours. The reaction mixture is then cooled and diluted with a suitable organic solvent, such as ethyl acetate. It is then filtered through Celite®, the filtrate is concentrated under vacuum, and the residue partitioned between ethyl acetate and water. The organic phase is separated, concentrated under vacuum, and the residue recrystallized from a suitable solvent mixture, such as acetone/water to provide the compound of formula I.

In Scheme III above, the compound of formula I may be contaminated with achiral dimer, (methylsulfonyl){2-[4-(4-{2-[(methylsulfonyl)amino]ethyl}phenyl)phenyl]ethyl}amine and chiral dimer, ((2R)-2-{4-[4-((1R)-1-methyl-2-{[(methylethyl)sulfonyl]amino}ethyl)phenyl]phenyl}propyl)[(methylethyl)sulfonyl]amine. It has been found that the above chiral dimer is more soluble than the compound of formula I in organic solvents and therefore, easily removed by recrystallization from such solvents. However, the above achiral dimer is less soluble in organic solvents than the compound of formula I therefore, generally resisted removal from the compound of formula I by recrystallization.

As shown in Table 1, entry 2 below, the addition of potassium formate (5 equivalents) into a deoxygenated reaction comprising palladium black, compound (13) and compound (6) provided an unexpected reduction of the achiral byproduct (0.14% reduced to 0.07%) relative to the deoxygenated reaction performed in the absence of potassium formate disclosed at entry 1.

TABLE 1

Effect of Formate on Achiral Dimer Formation

| Entry | Conditions | Catalyst | Additive | % achiral dimer in Compound I |
|---|---|---|---|---|
| 1 | Deoxygenated, under nitrogen | Pd (0) black (1.0 mol %) | No additive | 0.14 |
| 2 | Deoxygenated, under nitrogen | Pd (0) black (1.0 mol %) | Potassium formate (5.1 equivs) | 0.07 |

Table II discloses the effect of recrystallization solvents on the level of achiral dimer levels present with the compound of formula I.

TABLE II

| Entry | Solvent 1 | Solvent 2 | % Recovery[1] | % Achiral dimer present[2] |
|---|---|---|---|---|
| 1 | ethyl acetate | — | 66 | 1.05% |
| 2 | n-propanol | — | 92 | 1.02% |
| 3 | DMF | water | 85 | 0.84% |
| 4 | 3A ethanol | water | 87 | 1.23% |
| 5 | acetonitrile | water | 59 | 0.76% |
| 6 | water | — | 87 | 1.41% |
| 7 | acetone | water | 82 | 0.66% |
| 8 | DMSO | water | 75 | 1.04% |
| 9 | Isopropanol | water | 89 | 1.28% |
| 10 | methanol | water | 92 | 1.65% |
| 11 | n-propanol | water | 81 | 0.92% |
| 12 | toluene | — | 89 | 1.02% |
| 13 | MTBE | — | 95 | 1.08% |
| 14 | MIBK | — | 67 | 1.14% |
| 15 | THF | isopropanol | 47 | 1.49% |
| 16 | acetone | heptane | 58 | 0.87% |
| 17 | ethyl acetate | heptane | 91 | 1.07% |
| 18 | methylene chloride | heptane | 83 | 1.77% |

[1]Refers to % recovery of {(2R)-2-[4-(4-{2-[(methylsulfonyl)amino]ethyl}phenyl)phenyl]propyl}[(methylethyl)sulfonyl]amine.
[2]Refers to % of achiral dimer present with {(2R)-2-[4-(4-{2-[(methylsulfonyl)amino]ethyl}phenyl)phenyl]propyl}[(methylethyl)sulfonyl]amine after recrystallization from the indicated solvent.

Prior to recrystallization in Table II, 0.2 g of {(2R)-2-[4-(4-{2-[(methylsulfonyl)amino]ethyl}phenyl)phenyl]propyl}[(methylethyl)sulfonyl]amine was contaminated with 1.0% of the above achiral dimer. As disclosed in Table II a majority of the solvent combinations had no effect or actually increased the amount of achiral dimer present after recrystallization from the corresponding solvent system. Unexpectedly, entries 3, 5, 7 and 16 decreased the level of achiral dimer present with {(2R)-2-[4-(4-{2-[(methylsulfonyl)amino]ethyl}phenyl)phenyl]propyl}[(methylethyl)sulfonyl]amine.

More specifically, {(2R)-2-[4-(4-{2-[(methylsulfonyl)amino]ethyl}phenyl)phenyl]propyl}[(methylethyl)sulfonyl]amine contaminated with achiral dimer is dissolved in solvent 1 and precipitated slowly with addition of solvent 2. As used herein the term "suitable solvent system" refers to a mixture of solvents which removes achiral dimer from {(2R)-2-[4-(4-{2-[(methylsulfonyl)amino]ethyl}phenyl)phenyl]propyl}[(methylethyl)sulfonyl]amine upon recrystallization using the particular mixture of solvents. Examples of suitable solvent systems include DMF/water, acetonitrile/water, acetone/water, acetone/heptane, methyl ethyl keton/water, and the like.

Recrystallization of unrecrystallized compound of formula I from acetone/water affords enhanced purification, removing about 33% of the achiral dimer and about 28% of the chiral dimer from the compound of formula I. In addition, this recrystallization procedure provides finely divided compound of formula I at particle sizes between about 30 to about 35 microns (D50), thus facilitating formulation and oral absorption without recourse to milling.

Scheme IIIA

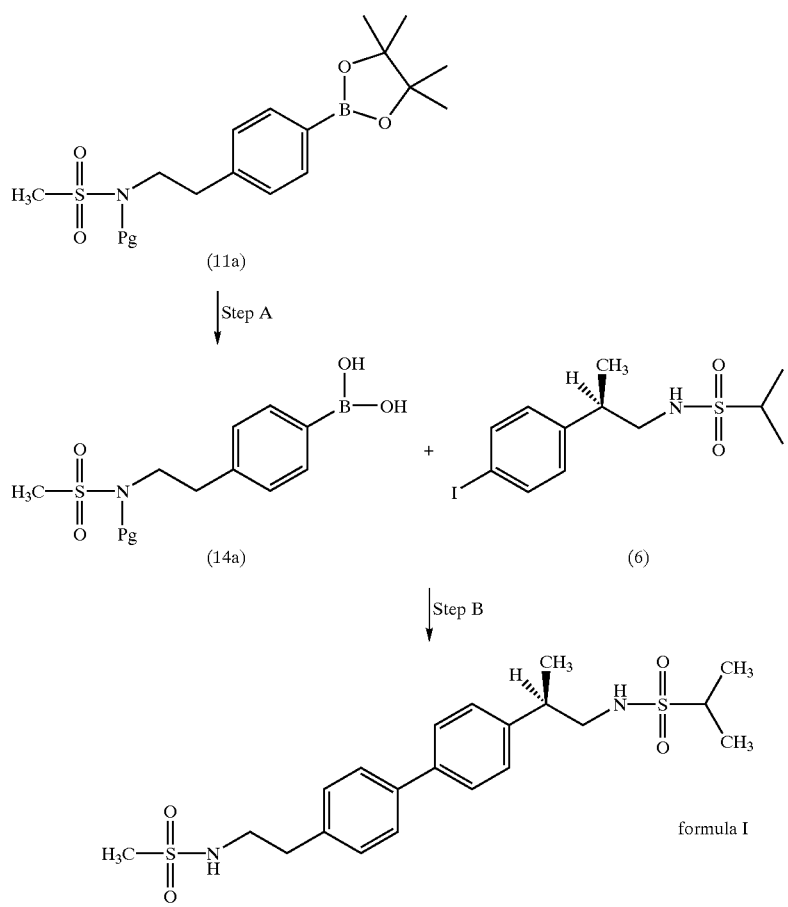

In Scheme IIIA, step A, compound (11a) is subjected to pinacolate cleavage to provide the compound (14a). Pg refers to refers to suitable protecting groups on the amine which are commonly employed to block or protect the amine while reacting other functional groups on the compound. Examples of suitable protecting groups used to protect the amino group and their preparation are disclosed by T. W. Greene, "Protective Groups in Organic Synthesis," John Wiley & Sons, 1981, pages 218–287. Choice of the suitable protecting group used will depend upon the conditions that will be employed in subsequent reaction steps wherein protection is required, and is well within the knowledge of one of ordinary skill in the art. Preferred protecting groups are t-butoxycarbonyl also known as a BOC protecting group, and benzyloxycarbonyl, also known as CBz. For example, compound (11a) is dissolved in a suitable organic solvent, such as acetone and added with stirring to an ammonium acetate solution to which an excess of sodium periodate has been added. The reaction mixture is allowed to stir for about 8 hours to about 16 hours and then it is concentrated under vacuum to remove the acetone. The aqueous phase is decanted from the oily product, and the aqueous is extracted with suitable organic solvents, such as methylene chloride and MTBE. The oily product and the organic extracts are combined and treated with aqueous base, such as sodium hydroxide, to provide a pH of about 12.5. The phases are separated and the organic phase is extracted with 1N sodium hydroxide and water. The aqueous phase and aqueous extracts were then combined and washed with suitable organic solvents, such as methylene chloride and MTBE. The aqueous is then added to a suitable organic solvent, such as methylene chloride and treated with a suitable acid, such as 1N sulfuric acid to provide a pH of about 3. The phases are separated and the aqueous phase is extracted with methylene chloride. The organic phase and organic extracts are combined and concentrated under vacuum. The residue is triturated with a suitable solvent mixture, such as MTBE/heptane to provide compound (14a).

In Scheme IIIA, step B, compound (14a) is coupled to compound (6) to provide the compound of formula I. For example compound (6) is combined with about 1.4 equivalents of compound (14a) and about 1.2 equivalents of potassium carbonate in a suitable organic solvent, such as n-propanol. To this mixture is added water, and a catalytic amount of palladium (II) acetate. The reaction mixture is then heated at reflux for about 20 hours. It is then cooled to room temperature and diluted with a suitable organic solvent, such as ethyl acetate. The diluted mixture is filtered through Celite® which is rinsed with ethyl acetate. The filtrates are combined, concentrated under vacuum and the residue diluted with a suitable organic solvent, such as ethyl acetate and 10% aqueous potassium carbonate. The phases are separated and the aqueous phase is extracted with ethyl acetate. The organic phase and organic extracts are combined, dried over anhydrous magnesium sulfate, filtered, and partially concentrated. The solution is heated to about 60° C. with stirring and a suitable organic solvent, such as heptane is added to provide a ratio by volume for ethyl acetate/heptane of about 17:11. The solution is allowed to cool slowly to room temperature with stirring for about 8 hours to about 16 hours and then cooled to about 0° C. The resulting solids are collected by filtration and rinsed with ethyl acetate/heptane to provide the compound of formula I.

The following examples are illustrative only and are not intended to limit the invention in any way. The reagents and starting materials are readily available to one of ordinary skill in the art. Unless indicated otherwise, the substituents are defined as hereinabove. As used herein, the following terms have the meanings indicated: "eq" refers to equivalents; "g" refers to grams; "mg" refers to milligrams; "ng" refers to nanograms; "L" refers to liters; "mL" refers to milliliters; "µL" refers to microliters; "mol" refers to moles; "mmol" refers to millimoles; "psi" refers to pounds per square inch; "kPa" refers to kilopascals; "min" refers to minutes; "h" refers to hours; "°C." refers to degrees Celsius; "TLC" refers to thin layer chromatography; "HPLC" refers to high performance liquid chromatography; "GC" refers to gas chromatography; "R$_f$" refers to retention factor; "δ" refers to part per million down-field from tetramethylsilane; "THF" refers to tetrahydrofuran; "DMF" refers to N,N-dimethylformamide; "DMSO" refers to methyl sulfoxide; "LDA" refers to lithium diisopropylamide; "aq" refers to aqueous; "iPrOAc" refers to isopropyl acetate; "EtOAc" refers to ethyl acetate; "MIBK" refers to methyl isobutyl ketone"; "EtOH" refers to ethyl alcohol; "MeOH" refers to methanol; "MTBE" refers to tert-butyl methyl ether; "DEAD" refers to diethyl azodicarboxylate; "TMEDA" refers to N,N,N',N'-tetramethylethylenediamine, and "RT" refers to room temperature.

EXAMPLE 1

Preparation of {(2R)-2-[4-(4-{2-[(methylsulfonyl) amino]ethyl}phenyl)phenyl]propyl}[(methylethyl) sulfonyl]amine

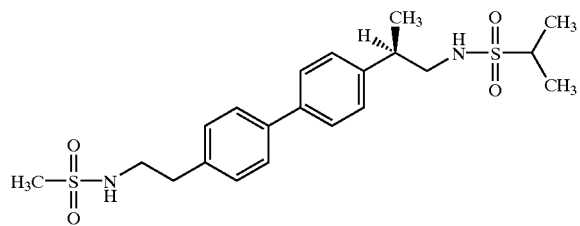

Preparation of 2-Phenyl-1-propylamine HCl

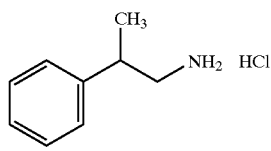

Scheme I, step A: To an autoclave hydrogenation apparatus under nitrogen was charged water-wet 5% palladium on carbon (453 g), ethanol (6.36 L), 2-phenylpropionitrile (636 g, 4.85 moles) and finally concentrated (12M) hydrochloric acid (613 g, 5.6 mole). The mixture was stirred rapidly and pressurized to 89.7–92.7 psi (618.46–639.15 kPa) with hydrogen. The mixture was then heated to 50–64° C. for 3 hours. $^1$H NMR analysis of an aliquot showed less than 5% starting material. The reaction mixture was depressurized and filtered to afford two lots of filtrate that were concentrated under reduced pressure to ~400 mL each. To each lot was added methyl tert-butyl ether (MTBE) (2.2 L each) and the precipitate solids were allowed to stir overnight. Each lot was filtered and the collected solids were each washed with fresh MTBE (100 mL) and dried overnight. The lots were combined to afford 2-phenyl-1-propylamine HCl (634.4 g, 76.2%) as a white powder.

$^1$H NMR analysis of the free base: $^1$H NMR (CDCl$_3$, 300 MHz) δ 7.32 (m, 2H), 7.21 (m, 3H), 2.86 (m, 2H), 2.75 (m, 1H), 1.25 (d, 3H, J=6.9), 1.02 (br s, 2H).

Preparation of (2R)-2-phenylpropylamine malate

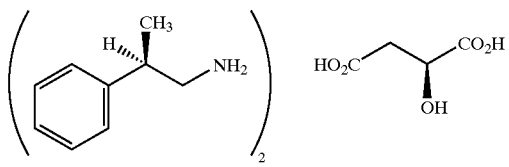

Scheme I, step B: To a dry 3-Liter round bottom flask under nitrogen was charged 2-phenyl-1-propylamine HCl (317.2 g, 1.85 moles), dry ethanol (2.0 L) and NaOH beads (75.4 g, 1.89 moles) that were washed in with additional ethanol (500 mL). The mixture was stirred for 1.6 hours, and the resulting milky white NaCl salts were filtered. An aliquot of the filtrate was analyzed by gas chromatography to provide the amount of free amine, 2-phenyl-1-propylamine, (1.85 moles). A solution of L-malic acid (62.0 g, 0.462 mole, 0.25 equivalents) in ethanol (320 mL) was added dropwise to the yellow filtrate and the solution was heated to 75° C. The solution was stirred at 75° C. for 30 minutes. The heat was removed and the solution was allowed to cool slowly. The resulting thick precipitate was allowed to stir overnight. The precipitate was filtered and dried under vacuum after rinsing with ethanol (325 mL) to afford (2R)-2-phenylpropylamine malate (147.6 g, 39.5%) as a white crystalline solid. Chiral GC analysis of the free base, 2-phenyl-1-propylamine revealed 83.2% e.e. enriched in the R-isomer (configuration was assigned via spectrometric comparison with commercial 2-phenyl-1-propylamine)

$^1$H NMR (CDCl$_3$, 300 MHz) δ 7.32 (m, 2H), 7.21 (m, 3H), 2.86 (m, 2H), 2.75 (m, 1H), 1.25 (d, 3H, J=6.9), 1.02 (br s, 2H).

A slurry of (2R)-2-phenylpropylamine malate (147.1 g, 83.2% e.e.) in 1325 mL ethanol and 150 mL deionized water was heated to reflux (~79.2° C.) until the solids went into solution. The homogeneous solution was allowed to slowly cool with stirring overnight. The precipitated white solids were cooled (0–5° C.) and filtered. The collected solids were rinsed with ethanol (150 mL) and dried at 35° C. to afford (2R)-2-phenylpropylamine malate (125.3 g, 85.2% recovery) as a white powder. Chiral GC analysis of the free base, (2R)-2-phenylpropylamine, revealed 96.7% e.e. enriched in the R-isomer.

$^1$H NMR (CD$_3$OD, 300 MHz) δ 7.32 (m, 10H), 4.26 (dd, 1H, J=3.6, 9.9), 3.08 (m, 6H), 2.72 (dd, 1H, J=9.3, 15.3), 2.38 (dd, 1H, J=9.3, 15.6), 1.33 (d, 6H, J=6.6).

Preparation of ((2R)-2-phenylpropyl)[(methylethyl)sulfonyl]amine

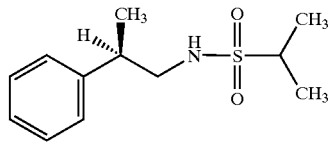

Scheme I, steps C and D: To a stirred slurry of (2R)-2-phenylpropylamine malate (200 g, 0.494 mol) in CH$_2$Cl$_2$ (1000 mL) was added 1.0 N NaOH (1050 mL, 1.05 moles). The mixture was stirred at room temperature for 1 hour and the organic phase was separated and gravity filtered into a 3.0 L round-bottom flask with a CH$_2$Cl$_2$ rinse (200 mL). The resulting free base, (2R)-2-phenylpropylamine, was dried via azeotropic distillation. Accordingly, the clear filtrate was concentrated to 600 mL at atmospheric pressure via distillation through a simple distillation head. Heptane (1000 mL) was added and the solution was concentrated again at atmospheric pressure to 600 mL using a nitrogen purge to increase the rate of distillation. The final pot temperature was 109° C.

The solution was cooled to room temperature under nitrogen with stirring to give a clear, colorless heptane solution (600 mL) of (2R)-2-phenylpropylamine. To this solution was added 4-dimethylaminopyridine (6.04 g, 0.0494 mol), triethylamine (200 g, 1.98 moles), and CH$_2$Cl$_2$ (500 mL). The mixture was stirred at room temperature until a clear solution was obtained. This solution was cooled to 5° C. and a solution of isopropylsulfonyl chloride (148 g, 1.04 moles) in CH$_2$Cl$_2$ (250 mL) was added dropwise with stirring over 2 hrs. The mixture was allowed to warm gradually to room temperature over 16 h. GC analysis indicated complete consumption of the (2R)-2-phenylpropylamine starting material.

The stirred mixture was cooled to 8° C. and 2 N HCl (500 mL) was added dropwise. The organic phase was separated and extracted with water (1×500 mL) and saturated NaHCO$_3$ (1×500 mL). The organic phase was isolated, dried (Na$_2$SO$_4$), and gravity filtered. The filtrate was concentrated under reduced pressure to provide ((2R)-2-phenylpropyl)[(methylethyl)sulfonyl]amine (230 g, 96%) as a pale yellow oil. $^1$H NMR (CDCl$_3$, 300 MHz) δ 7.34 (m, 2H), 7.23 (m, 3H), 3.89 (br t, 1H, J=5.4), 3.36 (m, 1H), 3.22 (m, 1H), 3.05 (m, 1H), 2.98 (m, 1H), 1.30 (d, 3H, J=7.2), 1.29 (d, 3H, J=6.9), 1.25 (d, 3H, J=6.9).

Preparation of [(2R)-2-(4-iodophenyl)propyl][methylethyl)sulfonyl]amine

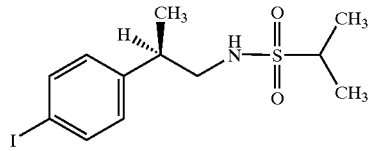

Scheme I, step E: A stirred room temperature solution of ((2R)-2-phenylpropyl)[(methylethyl)sulfonyl]amine (37.1 g, 0.154 mol) in glacial acetic acid (185 mL) was treated with concentrated H$_2$SO$_4$ (16.0 g, 0.163 mol), added dropwise in a slow stream, followed by a H$_2$O rinse (37 mL). To this solution (~30° C.) was added H$_5$IO$_6$ (8.29 g, 0.0369 mol), followed by iodine (17.9 g, 0.0707 mol). The resulting reaction mixture was heated and allowed to stir for 3 h at 60° C. After HPLC analysis verified the consumption of starting material, the reaction mixture was cooled to 30° C. and a 10% aqueous solution of NaHSO$_3$ (220 mL) was added dropwise while maintaining the temperature between 25° C. and 30° C. The mixture crystallized to a solid mass upon cooling to 0–5° C.

The solids were suction filtered and rinsed with H$_2$O to afford 61.7 g of crude solids that were redissolved into warm MTBE (500 mL). This solution was extracted with H$_2$O (2×200 mL) and saturated NaHCO$_3$ (1×200 mL) and the organic phase was dried (MgSO$_4$), filtered, and concentrated under reduced pressure to ~200 mL. Heptane (100 mL) was added dropwise to the product solution with slow stirring until crystallization commenced. An additional 100 mL of heptane was added and the resulting suspension was allowed to stir slowly overnight at room temperature. The mixture was then cooled (0° C.), filtered, and the collected solids were rinsed with heptane. The solids were then air-dried to afford the intermediate title compound, [(2R)-2-(4-iodophenyl)propyl][(methylethyl)sulfonyl]amine (33.7 g, 59.8%) as a white powder. Chiral Chromatography of this lot indicated 100% e.e.

$^1$H NMR (CDCl$_3$, 300 MHz) δ 7.66 (d, 2H, J=8.1), 6.98 (d, 2H, J=8.4), 3.86 (br t, 1H, J=5.1), 3.33 (m, 1H), 3.18 (m, 1H), 3.06 (m, 1H), 2.92 (m, 1H), 1.30 (d, 3H, J=6.6), 1.27 (d, 6H, J=6.6).

Preparation of (methylsulfonyl)(2-phenylethyl)amine

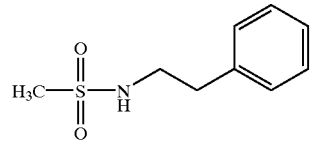

Scheme II, step A: To a 10° C. solution of phenethylamine (12.1 g, 0.100 mol) and triethylamine (11.1 g, 0.110 mol) in CH$_2$Cl$_2$ (50 mL) was added methanesulfonyl chloride (12.6 g, 0.110 mol) dropwise over 10 min. The solution was stirred at room temperature for 1.5 h and was then washed with 1N HCl (5×20 mL). The organic phase was directly concentrated to provide the intermediate title compound, (methylsulfonyl)(2-phenylethyl)amine, (21.2 g, 93.3%) as an oil.

$^1$H NMR (CDCl$_3$, 300 MHz) δ7.32 (m, 2H), 7.23 (m, 3H), 4.30 (br s, 1H), 3.40 (t, 2H, J=3.9), 2.88 (t, 2H, J=4.2), 2.81 (s, 3H).

Preparation of [2-(4-iodophenyl)ethyl](methylsulfonyl)amine

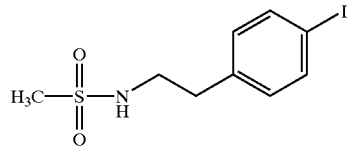

Scheme II, step B: To a stirring room temperature solution of (methylsulfonyl)(2-phenylethyl)amine (205 g, 1.03 moles), water (200 mL), 95% sulfuric acid (111 g, 1.08 moles) in acetic acid (1 L), was added iodine (111 g, 0.438 mol) and periodic acid (H$_5$IO$_6$, 45.6 g, 0.206 mol). The reaction mixture was warmed to 70–75° C. for 3 h. The heat was removed and the dark violet reaction mixture was allowed to proceed overnight at room temperature. Potassium hydroxide pellets (85%, 143 g, 2.16 moles) were added to neutralized the sulfuric acid and then enough saturated aqueous sodium sulfite was added to decolorize the mixture to afford a white suspension. The suspension was cooled to 15° C. and filtered. The filter cake was triturated thoroughly with water and was then dissolved in $CH_2Cl_2$ (1 L) and extracted with additional water (2×200 mL). The organic phase was concentrated under reduced pressure to provide the intermediate title compound, [2-(4-iodophenyl)ethyl](methylsulfonyl)amine, (201 g, 60.2%) as a white powder.

$^1$H NMR (CDCl$_3$, 300 MHz) δ 7.64 (d, 2H, J=4.8), 6.97 (d, 2H, J=5.1), 4.37 (br t, 1H, J=4), 3.36 (app. q, 2H, J=3.9), 2.85 (s, 3H), 2.82 (t, 2H, J=3.9).

Preparation of (tert-butoxy)-N-[2-(4-iodophenyl)ethyl]-N-(methylsulfonyl)carboxamide

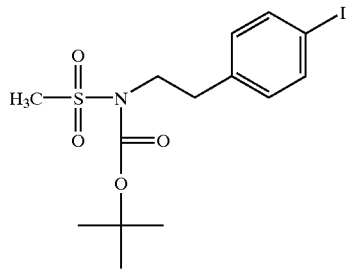

Scheme II, step C: A room temperature solution of [2-(4-iodophenyl)ethyl](methylsulfonyl)amine (201 g, 0.618 mol), 4-dimethylaminopyridine (3.8 g, 0.031 mol) and di-tert-butyl dicarbonate (162 g, 0.744 mol) in $CH_2Cl_2$ (1 L) was allowed to stir overnight. The reaction mixture was washed with water (2×400 mL) and the organic phase was concentrated to about 600 mL and hexanes (400 mL) was added. This combined solution was washed again with water (400 mL) and was concentrated to a solid that was suspended in hexanes (600 mL) and filtered. The collected solids were dried under reduced pressure to afford the intermediate title compound, (tert-butoxy)-N-[2-(4-iodophenyl)ethyl]-N-(methylsulfonyl)carboxamide (241.5 g, 91.5%) as a white solid.

$^1$H NMR (CDCl$_3$, 300 MHz) δ 7.63 (d, 2H, J=7.8), 6.98 (d, 2H, J=7.8), 3.88 (t, 2H, J=6.9), 3.10 (s, 3H), 2.88 (t, 2H, J=6.9), 1.51 (s, 9H).

Preparation of (tert-butoxy)-N-(methylsulfonyl)-N-{2-[4-(4,4,5,5-tetramethyl(1,3,2-dioxaborolan-2-yl))phenyl]ethyl}carboxamide

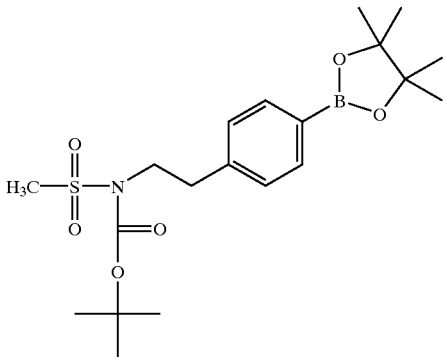

Scheme II, step D: To a degassed solution of (tert-butoxy)-N-[2-(4-iodophenyl)ethyl]-N-(methylsulfonyl)carboxamide (128 g, 0.300 mol), triethylamine (91.1 g, 0.900 mol), and 1,1'-bis(diphenylphosphino) ferrocenedichloropalladium (II)-$CH_2Cl_2$ complex (2.9 g, 0.0035 mol) in acetonitrile (600 mL) was added pinacolborane (50 g, 0.391 mol) dropwise. The mixture was stirred at 70–74° C. for 8 h and then was cooled to room temperature. The reaction mixture was concentrated to a fluid oil that was partitioned between MTBE (500 mL) and water (500 mL). The organic phase was separated and washed with water (2×200 mL) and concentrated to a residue that was partially dissolved with heptane (1 L). The heptane soluble fraction was filtered through Celite® 521 and concentrated to an oil (95 g). The residue was dissolved in acetone (600 mL) and heptane (600 mL) and filtered through Celite® 521. The combined filtrates were concentrated to 95 g of a mixture of a 3:1 molar ratio ($^1$H NMR, 81.0% by weight) of intermediate title compound, (tert-butoxy)-N-(methylsulfonyl)-N-{2-[4-(4,4,5,5-tetramethyl(1,3,2-dioxaborolan-2-yl))phenyl]ethyl}carboxamide, (60.3% potency corrected yield) and protio derivative.

$^1$H NMR (CDCl$_3$, 300 MHz) δ 7.75 (d, 2H, J=7.8), 7.23 (d, 2H, J=8.1), 3.87 (t, 2H, J=8.1), 2.99 (s, 3H), 2.90 (t, 2H, J=7.5), 1.53 (s, 9H), 1.33 (s, 6H), 1.27 (s, 6H).

Preparation of (methylsulfonyl){2-[4-(4,4,5,5-tetramethyl(1,3,2-dioxaborolan-2-yl))phenyl]ethyl}amine

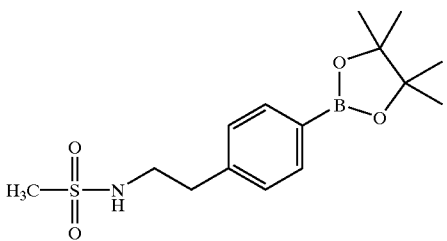

Scheme II, step E: To a 2 L flask charged with a stirring solution of (tert-butoxy)-N-(methylsulfonyl)-N-{2-[4-(4,4,5,5-tetramethyl(1,3,2-dioxaborolan-2-yl))phenyl]

ethyl}carboxamide (98.7 g, 0.232 mol) in $CH_2Cl_2$ (500 mL) was added trifluoroacetic acid (82 mL, 121.4 g, 1.06 moles) dropwise from an addition funnel. No exotherm was observed and the reaction solution was allowed to stir at room temperature for 18 h.

HPLC analysis indicated 98% completion so the cooled (5° C.) reaction mixture was neutralized by the slow addition of 5N NaOH (175 mL). The pH of the aqueous phase was 10.5. The phases were separated and the aqueous phase was extracted with $CH_2Cl_2$ (50 mL). The combined $CH_2Cl_2$ phases were washed with brine (2×100 mL) and water (1×100 mL). The $CH_2Cl_2$ phase was diluted with heptane (300 mL) and was concentrated under reduced pressure to afford a suspension that was isolated by filtration. The collected solids were washed with pentane (2×100 mL) and dried under vacuum to provide the intermediate title compound, (methylsulfonyl){2-[4-(4,4,5,5-tetramethyl(1,3,2-dioxaborolan-2-yl))phenyl]ethyl}amine, (69.0 g, 91.4%) as a white powder.

$^1$H NMR (CDCl$_3$, 300 MHz) δ 7.77 (d, 2H, J=8.1), 7.22 (d, 2H, J=7.8), 4.26 (br t, 1H, J=6), 3.40 (q, 2H, J=6.9), 2.89 (t, 2H, J=6.6), 2.82 (s, 3H), 1.34 (s, 12H).

Preparation of 4-{2-[(methylsulfonyl)amino]ethyl}benzene boronic acid

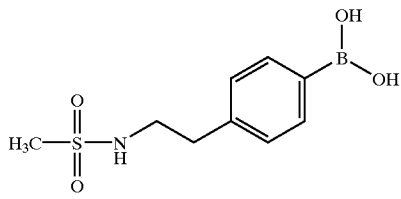

Scheme II, step F: (Methylsulfonyl){2-[4-(4,4,5,5-tetramethyl(1,3,2-dioxaborolan-2-yl))phenyl]ethyl}amine (68.0 g, 0.209 mol) was placed into a 2 L flask and combined with acetone (600 mL), 1N ammonium acetate (600 mL), and NaIO$_4$ (168.1 g, 0.786 mol). This mixture was stirred at room temperature overnight. The reaction mixture was filtered to remove insoluble matter to afford filtrate A. The collected solids were washed with acetone (2×100 mL) and this filtrate was combined with filtrate A. The combined filtrates were concentrated under reduced pressure to 600 mL to afford a precipitate that was recovered by filtration. The collected solids were air-dried to give 110 g of crude material. This crude material was suspended in water (100 mL) and 5N NaOH was added until the pH was 12.5. The resulting suspension was filtered and the filtrate was treated with decolorizing carbon (Darco 6-60). The mixture was filtered and the filtrate was diluted with 10N $H_2SO_4$ until the pH was 5.0 to precipitate the intermediate title compound. This precipitate was collected by filtration and dried under reduced pressure to provide the intermediate title compound, 4-{2-[(methylsulfonyl)amino]ethyl}benzene boronic acid, (41.9 g, 82.5%) as a white powder.

$^1$H NMR (acetone-d$_6$, 300 MHz) δ 7.82 (d, 2H, J=8.4), 7.27 (d, 2H, J=7.8), 7.11 (s, 2H), 6.03 (m, 1H), 3.36 (m, 2H), 2.91 (m, 2H), 2.84 (s, 3H).

Preparation of Final Title Compound

Scheme III: An aqueous solution of potassium formate was prepared in the following manner. To 15 mL of water was added KOH (85% flakes, 6.73 g, 0.102 mol), then 98% formic acid (4.70 g, 0.102 mol). Alternatively, one may use commercially available potassium formate. To this solution was then added $K_2CO_3$ (2.76 g, 0.0210 mol), 4-{2-[(methylsulfonyl)amino]ethyl}benzene boronic acid (4.62 g, 0.190 mol), 1-propanol (100 mL), and [(2R)-2-(4-iodophenyl)propyl][(methylethyl)sulfonyl]amine (7.35 g, 0.200 mol). This mixture was deoxygenated via three vacuum/N$_2$-refill cycles. Palladium black (0.0215 g, 0.0002 mol) was added and the mixture was again deoxygenated via three vacuum/N$_2$-refill cycles. The reaction flask was heated in a preheated oil bath at 88° C. and the mixture was stirred overnight.

HPLC analysis showed complete consumption of 4-{2-[(methylsulfonyl)amino]ethyl}benzene boronic acid, and the mixture was diluted with ethyl acetate and filtered through Celite® to remove palladium. The mixture was concentrated under reduced pressure and the resulting residue was partitioned between ethyl acetate and water. The organic phase was concentrated and the solid residue was collected and recrystallized from 1:1 acetone/water to afford the final title compound, {(2R)-2-[4-(4-{2-[(methylsulfonyl)amino]ethyl}phenyl)phenyl]propyl}[(methylethyl)sulfonyl]amine, (6.2 g, 75%) as a white crystalline powder.

$^1$H NMR (CDCl$_3$, 300 MHz) δ 7.54 (dd, 4H, J=1.8, 8.1), 7.29 (dd, 4H, J=1.8, 8.1), 4.27 (t, 1H, J=6.6), 3.91 (m, 1H), 3.43 (q, 2H, J=6.6), 3.37 (dd, 1H, J=5.7, 7.5), 3.26 (m, 1H), 3.07 (m, 2H), 2.93 (t, 2H, J=6.6), 2.87 (s, 3H), 1.34 (d, 3H, J=7.2), 1.31 (d, 3H, J=6.9), 1.27 (d, 3H, J=6.6).

Additional Procedure for Preparation of Final Title Compound.

Scheme III: Within a single-neck, 3 L round bottom flask equipped with a magnetic stir bar was placed potassium formate (112.8 g, 1.34 moles, 5.1 eq) and water (200 mL) to provide a pH 8 solution. Potassium carbonate (72.7 g, 0.526 mol, 2.0 eq), and 4-{2-[(methylsulfonyl)amino]ethyl}benzene boronic acid (60.8 g, 0.250 mol, 0.95 eq) was added to form a stirring suspension as 1-propanol (720 mL) was added. [(2R)-2-(4-iodophenyl)propyl][(methylethyl)sulfonyl]amine (96.6 g, 0.263 mol, 1.0 eq) was added followed by additional 1-propanol (600 mL). The resulting mixture was stirred for 3 minutes while the reaction flask was fitted with a heating mantle and a glycol-cooled reflux condenser. Vacuum (10–20 torr) was slowly applied to the system over 10 minutes. Stirring had stopped due to the additional precipitation of the cooled system; nevertheless, after 30 minutes, the system was returned to atmospheric pressure with nitrogen. With gentle heating, the flask was evacuated and refilled with nitrogen two additional times. Stirring was stopped and palladium black (0.28 g, 0.0026 mol, 0.01 eq) was quickly added to the flask. Stirring was resumed and the system was again evacuated and returned to atmospheric pressure with nitrogen over a 2 minute cycle. This evacuation/nitrogen purge was repeated two more times over a 15 second cycle and the mixture was heated to reflux.

After 16 hours, an aliquot was removed and analyzed by HPLC (275 nm detection). Analysis showed 0.07% of achiral dimer, (methylsulfonyl){2-[4-(4-{2-[(methylsulfonyl)amino]ethyl}phenyl)phenyl]ethyl}amine, relative to the desired product, {(2R)-2-[4-(4-{2-[(methylsulfonyl)amino]ethyl}phenyl)phenyl]propyl}[(methylethyl)sulfonyl]amine. The reaction mixture was cooled to 50° C. and ethyl acetate (500 mL) was added. The reaction mixture was then cooled to room temperature and the product, {(2R)-2-[4-(4-{2-[(methylsulfonyl)amino]ethyl}phenyl)phenyl]propyl}[(methylethyl)sulfonyl]amine, began to precipitate. Additional ethyl acetate (1 L) was introduced to redissolve the product and the upper organic phase was decanted and filtered through Celite® to remove palladium metal. The filter cake was rinsed with 1-propanol. The homogeneous filtrate was concentrated under reduced pressure to remove n-propanol and after removal of 1.5 L of distillate, the product suspension was filtered. The combined filter cakes were dried to afford 109.8 g of crude final title compound.

Recrystallization. The crude final title compound (109.8 g) was dissolved in acetone (490 mL). This solution was filtered though a glass filter to retain a minor amount of dark insoluble material. To the slowly stirred filtrate was added water (300 mL) over 15 min. The resulting suspension was stirred for 15 minutes and additional water (20 mL) was introduced over 10 minutes. The suspension was subsequently stirred for 30 minutes at room temperature and was filtered. The cake was washed with 1:1 acetone/water (600 mL) and was dried at 35° C. overnight. This process afforded 80.3 g (81.1%) of {(2R)-2-[4-(4-{2-[(methylsulfonyl)amino]ethyl}phenyl)phenyl]propyl}[(methylethyl)sulfonyl]amine as a white crystalline powder. HPLC analysis indicated 0.01% achiral dimer, (methylsulfonyl){2-[4-(4-{2-[(methylsulfonyl)amino]ethyl}phenyl)phenyl]ethyl}amine, and 0.02% chiral dimer, ((2R)-2-{4-[4-((1R)-1-methyl-2-{[(methylethyl)sulfonyl]amino}ethyl)phenyl]phenyl}propyl)[(methylethyl)sulfonyl]amine.

The above recrystallization procedure reproducibly provided {(2R)-2-[4-(4-{2-[(methylsulfonyl)amino]ethyl}phenyl)phenyl]propyl}[(methylethyl)sulfonyl]-amine with an unexpectedly low mean particle size distribution of about 29 microns to about 34 microns in the unmilled state. In view of the poor water solubility of {(2R)-2-[4-(4-{2-[(methylsulfonyl)amino]ethyl}phenyl)phenyl]-propyl}[(methylethyl)sulfonyl]amine, this low particle size greatly facilitates formulation and oral absorption in animals without recourse to milling.

EXAMPLE 2

Preparation of 4-{2-[(tert-butoxy)-N-(methylsulfonyl)carbonylamino]ethyl}benzene boronic acid

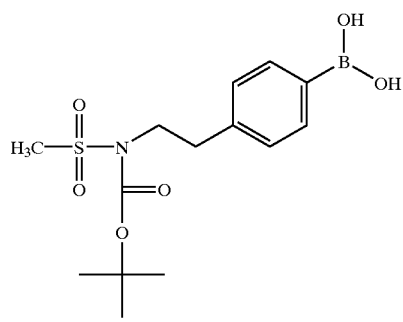

Scheme IIIA, step A: To a room temperature solution of (tert-butoxy)-N-(methylsulfonyl)-N-{2-[4-(4,4,5,5-tetramethyl(1,3,2-dioxaborolan-2-yl))phenyl]ethyl}carboxamide (81.0% potent, 95 g, 0.18 mol, prepared in example 1) in acetone (2 L) was added 1N ammonium acetate (1 L) and sodium periodate (145 g, 0.678 mol) with stirring. The reaction was allowed to proceed overnight. The reaction mixture was concentrated to remove the acetone, and the aqueous phase was decanted away from the oily product. The aqueous phase was extracted with $CH_2Cl_2$ (100 mL) and MTBE (2×100 mL). The combined oily product and organic phases were adjusted to pH 12.5 with the addition of 1 N NaOH. The phases were separated, and the organic phase was extracted with 1 N NaOH (100 mL) and water (2×100 mL). HPLC analysis (60% $CH_3CN$/40% $H_2O$, 2 mL/min, Zorbax C-18, 205 nm) of the organic phase indicated that the product had been removed from this phase. The aqueous phases (containing product) were finally combined and washed with $CH_2Cl_2$ (100 mL) and MTBE (2×100 mL). The aqueous phase was added to $CH_2Cl_2$ (450 mL) and 1 N $H_2SO_4$ was added until the aqueous phase was at pH 3.05. The phases were separated and the aqueous phase was extracted with $CH_2Cl_2$ (100 mL). The combined organic extracts (containing product) were concentrated to an oil (58.5 g) that crystallized overnight. The resulting solid mass was triturated with 10% MTBE in heptane (100 mL) to afford, after filtration and drying under reduced pressure, the intermediate title compound, 4-{2-[(tert-butoxy)-N-(methylsulfonyl)carbonyl-amino]ethyl}benzene boronic acid, (47.7 g, 77.2%) as a white powder.

$^1$H NMR ($d_6$-DMSO, 300 MHz) δ 7.83 (d, 2H, J=4.8), 7.24 (d, 2H, J=5.1), 7.12 (s, 2H), 3.90 (t, 2H, J=3.9), 3.12 (s, 3H), 2.95 (t, 2H, J=4.5), 1.52 (s, 9H).

We claim:

1. A process for the preparation of a biphenyl compound comprising combining a phenyl boronic acid derivative with a suitable benzene derivative in the presence of a suitable additive selected from the group consisting of hydrogen, hydroquinone, isopropanol, sodium formate, potassium formate, tetralkylammonium formate in a suitable organic solvent with a suitable catalyst and a suitable base.

2. A process according to claim 1 further comprising heating the mixture to a temperature of from about 30° C. to about 95° C. for about 3 hours to about 20 hours.

3. A process according to claim 2 wherein the suitable catalyst is a palladium (0) catalyst.

4. A process according to claim 3 wherein the suitable additive is sodium formate or potassium formate.

5. A process according to claim 4 wherein the suitable solvent is methanol, ethanol, isopropanol, or n-propanol.

6. A process according to claim 5 wherein the suitable base is potassium carbonate or sodium carbonate.

7. A process according to claim 5 wherein the suitable base is potassium carbonate.

8. A process according to claim 7 wherein the suitable benzene derivative is an iodobenzene derivative.

9. A process for the preparation of a compound of formula:

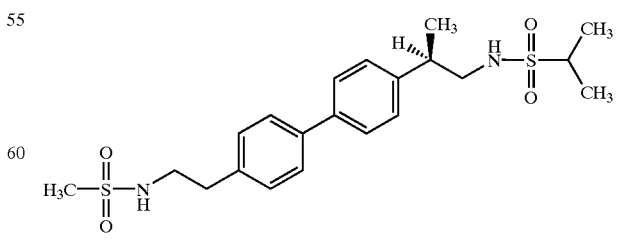

comprising combining a compound of the formula (13):

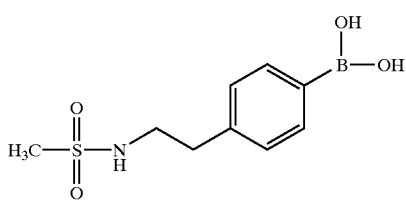

with a compound of the formula (6):

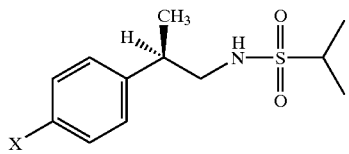

wherein X represents Cl, Br, I, or triflate, in the presence of a suitable additive selected from the group consisting of hydrogen, hydroquinone, isopropanol, sodium formate, potassium formate, tetralkylammonium formate in a suitable organic solvent with a suitable catalyst and a suitable base.

10. A process according to claim 9 wherein the suitable organic solvent is chosen from methanol, ethanol, isopropanol, n-propanol, butanol, tetrahydrofuran, acetone, or butanone.

11. A process according to claim 10 wherein the suitable catalyst is palladium black.

12. A process according to claim 11 wherein the suitable base is potassium carbonate.

13. A process according to claim 12 wherein the mixture is heated at a temperature of from about 30° C. to about 90° C. for about 3 hours to about 20 hours.

14. A process according to claim 13 wherein X is I.

15. A process as according to claim 13 wherein X is Br.

16. A process for the preparation of a compound of formula:

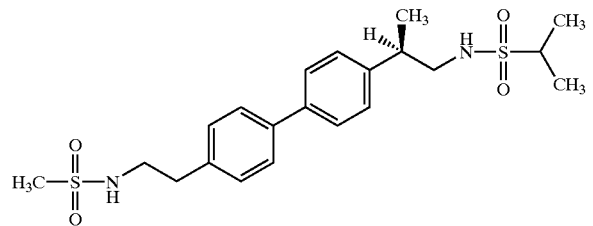

comprising combining a compound of the formula (13):

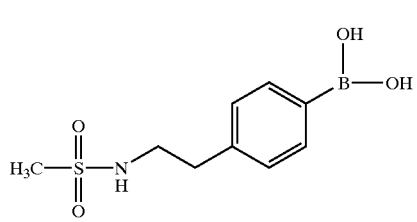

with a compound of the formula (6):

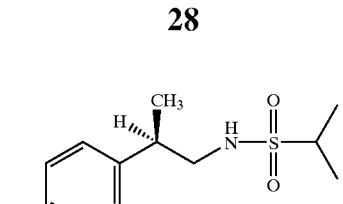

in the presence of aqueous potassium formate, n-propanol, palladium black; potassium carbonate, and heating the reaction mixture at about 88° C. for about 8 hours.

17. A process for the preparation of a compound of formula:

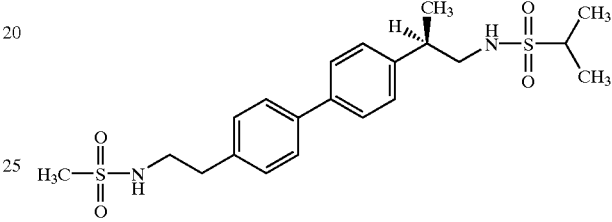

comprising combining a compound of the formula (14a):

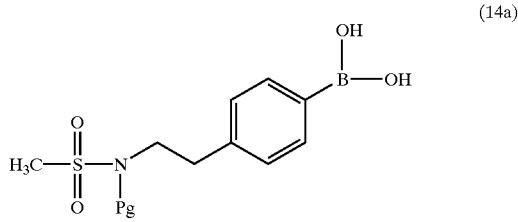

wherein Pg represents a suitable protecting group, with a compound of the formula (6):

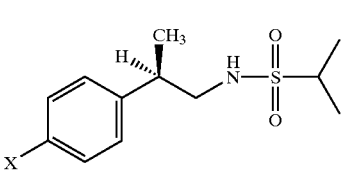

wherein X represents Cl, Br, I or triflate in the presence of a suitable additive selected from the group consisting of hydrogen, hydroquinone, isopropanol, sodium formate, potassium formate, tetralkylammonium formate in a suitable organic solvent with a suitable catalyst and a suitable base.

* * * * *